United States Patent
Wong et al.

(10) Patent No.: US 9,865,080 B2
(45) Date of Patent: Jan. 9, 2018

(54) VELOCITY VOLUME RENDERING WITH SIGN-BASED TERMINATION IN ULTRASOUND

(71) Applicant: Siemens Medical Solutions USA, Inc., Malvern, PA (US)

(72) Inventors: King Yuen Wong, Issaquah, WA (US); Mervin Mencias Smith-Casem, Renton, WA (US)

(73) Assignee: SIEMENS MEDICAL SOLUTIONS USA, INC., Malvern, PA (US)

( * ) Notice: Subject to any disclaimer, the term of this patent is extended or adjusted under 35 U.S.C. 154(b) by 440 days.

(21) Appl. No.: 14/484,056

(22) Filed: Sep. 11, 2014

(65) Prior Publication Data

US 2016/0078668 A1    Mar. 17, 2016

(51) Int. Cl.
| | |
|---|---|
| *G06T 15/08* | (2011.01) |
| *G06T 15/06* | (2011.01) |
| *A61B 8/06* | (2006.01) |
| *A61B 8/08* | (2006.01) |
| *A61B 8/00* | (2006.01) |
| *G01S 15/89* | (2006.01) |

(52) U.S. Cl.
CPC ............... *G06T 15/08* (2013.01); *A61B 8/06* (2013.01); *A61B 8/483* (2013.01); *A61B 8/488* (2013.01); *G01S 15/8993* (2013.01); *G06T 15/06* (2013.01); *A61B 8/463* (2013.01); *G01S 15/8984* (2013.01); *G06T 2210/41* (2013.01)

(58) Field of Classification Search
None
See application file for complete search history.

(56) References Cited

U.S. PATENT DOCUMENTS

| | | | | |
|---|---|---|---|---|
| 6,503,202 | B1* | 1/2003 | Hossack | A61B 8/13 600/454 |
| 2002/0190984 | A1* | 12/2002 | Seiler | G06T 15/005 345/424 |
| 2006/0173326 | A1* | 8/2006 | Thiele | A61B 8/06 600/440 |
| 2007/0014446 | A1* | 1/2007 | Sumanaweera | G06T 15/08 382/128 |
| 2007/0066896 | A1* | 3/2007 | Simopoulos | G01S 15/584 600/437 |
| 2008/0024515 | A1* | 1/2008 | Yang | G06T 15/06 345/592 |

(Continued)

OTHER PUBLICATIONS

Y.M. Yoo, et al., "New multi-volume rendering technique for three-dimensional power Doppler imaging," Ultrasonics 46, pp. 313-322, 2007.

(Continued)

*Primary Examiner* — Andrew G Yang

(57) ABSTRACT

Velocities are volume rendered in ultrasound. Early ray termination is used to avoid compositing velocities of different signs together. As long as the velocities are of the same sign, compositing continues from the viewer to a back of the volume being rendered. Once the velocity changes sign, compositing is reduced or terminated to avoid compositing velocities of different directions. The velocity rendering emphasizes the velocities of one direction closest to the viewer.

19 Claims, 4 Drawing Sheets
(3 of 4 Drawing Sheet(s) Filed in Color)

(56) References Cited

U.S. PATENT DOCUMENTS

| | | | | |
|---|---|---|---|---|
| 2010/0201685 A1* | 8/2010 | Mortimer | ............... | G06T 15/08 345/424 |
| 2011/0137156 A1* | 6/2011 | Razzaque | .............. | A61B 34/20 600/424 |
| 2012/0069020 A1* | 3/2012 | Smith-Casem | ......... | G06T 15/08 345/426 |

OTHER PUBLICATIONS

Y. Luo, "Effectively Visualizing the Spatial Structure of Cerebral Blood Vessels," Computing in Science & Engineering, pp. 41-46, Mar./Apr. 2013.

Y. Yoo, "P3A-1 Directional Fusion-based Multi-Volume Rendering Technique for 3D Color Doppler Imaging," 2006 IEEE Ultrasonics Symposium, pp. 1975-1978, 2006.

* cited by examiner

วELOCITY VOLUME RENDERING WITH SIGN-BASED TERMINATION IN ULTRASOUND

BACKGROUND

The present embodiments relate to medical diagnostic imaging. In particular, volume imaging of velocity is provided.

Color Doppler velocity data contains information about both the magnitude and direction of flow. During volume rendering color Doppler velocity data, samples of color Doppler velocity data are interpolated and composited together along viewing rays. Compositing velocity data with different signs may cause the flow direction of the composited result to be ambiguous or unexpected. For example, if the compositing operates on post-color-mapped (RGBA) samples, hues representative of positive and negative flows (e.g., reddish and bluish hues) mix to produce magenta-hued colors. The direction of magenta is ambiguous as the user expects reddish or bluish for towards and away from the transducer. If the compositing operates on pre-color-mapped velocity data, compositing positive and negative data may lead to no flow at all as the compositing causes the flow velocities along the ray to cancel each other out.

BRIEF SUMMARY

By way of introduction, the preferred embodiments described below include methods, computer-readable media and systems for volume rendering velocities in ultrasound. Early ray termination is used to avoid compositing velocities of different signs together. As long as the velocities are of the same sign, compositing continues from the viewer to a back of the volume being rendered. Once the velocity changes sign, compositing is reduced or terminated to avoid compositing velocities of different directions. The velocity rendering emphasizes the velocities of one direction closest to the viewer.

In a first aspect, a method is provided for volume rendering in ultrasound. Estimates of velocity at different locations distributed in three-dimensions in a patient are obtained. The estimates are signed for the velocity to and away from an ultrasound transducer. The estimates are composited along ray lines in a front to back direction relative to a viewer in three-dimensional rendering. During the compositing in the front to the back direction for at least one of the ray lines, a change in sign of the estimates is detected. Contribution of the estimates beyond the change in sign to the compositing is reduced in response to the detecting of the change. A velocity image is generated from the three-dimensional rendering.

In a second aspect, a system is provided for volume rendering in ultrasound. A memory is operable to store velocities representing voxels in a volume of a patient. A processor is configured to volume render an image of pixels from the velocities where contribution for each pixel from velocities of the volume is limited to the velocities of a same sign. A display is operable to display the image.

In a third aspect, a non-transitory computer readable storage medium has stored therein data representing instructions executable by a programmed processor for volume rendering in ultrasound. The storage medium includes instructions for: directly volume rendering directional flow data; detecting a flow direction change for directional flow data having a contribution to the volume rendering above a threshold; and stopping compositing of the directional flow data in the direct volume rendering when the flow direction change for the contribution above the threshold is detected.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND SPECIFIC EMBODIMENTS

Color Doppler velocity volume rendering is enhanced. During direct volume rendering of color Doppler velocity data or other directional data, the compositing of the data is stopped when a direction change is detected along the ray. Non-color Doppler velocity data may continue to be composited. Ambiguous or unexpected flow direction indication is reduced by stopping the compositing of color Doppler data when a significant change in flow direction along the viewing direction is detected. Processing time may be saved by early termination.

Figure 1:
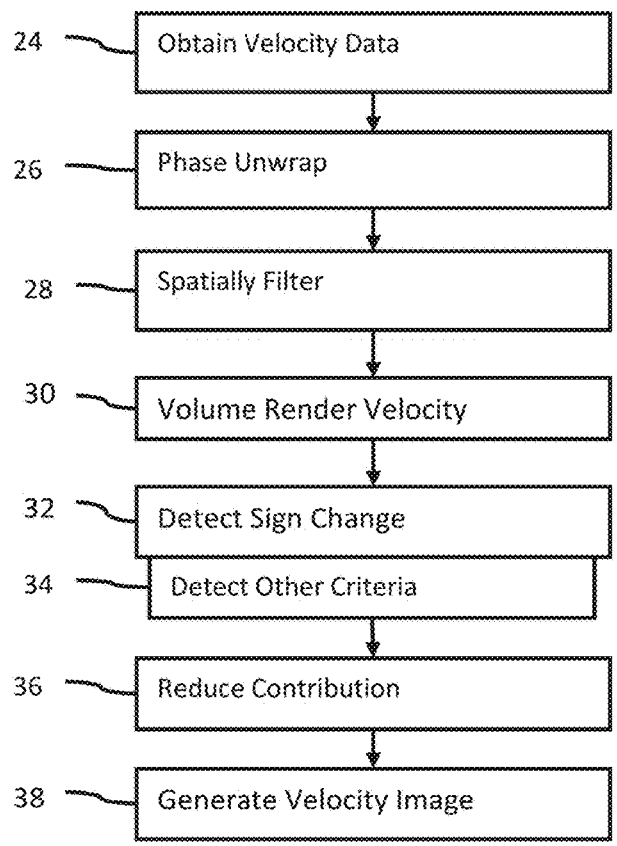
FIG. 1 is a flow chart of one embodiment of a method for volume rendering velocities in ultrasound.

FIG. 1 shows one embodiment of a method for volume rendering in ultrasound. The method is implemented by a medical diagnostic imaging system, a review station, a workstation, a computer, a PACS station, a server, combinations thereof, or other device for image processing medical ultrasound or other types of volume data. For example, the system 10 or computer readable media 14 and processor 12 shown in FIG. 7 implement the method, but other systems may be used.

The method is implemented in the order shown or a different order. For example, acts 26 and 28 may be reversed or performed simultaneously. As another example, act 34 is performed before or as part of act 32. Additional, different, or fewer acts may be performed. For example, acts 26, 28, and/or 34 are not performed. As another example, acts associated with operations by the user are included, such as positioning the transducer, activation of the process and/or input of view direction for rendering. In yet another example, act 38 is not performed and the rendered image is instead stored or transmitted.

The acts 24-38 are performed in real-time, such as during scanning. The user may view images while scanning. For real-time imaging, the volume data used for any given rendering may be replaced with more recently acquired data. For example, an initial rendering is performed with one set of data. The final rendering is performed with another set of data representing the same or similar (e.g., due to transducer or patient movement) volume. In alternative embodiments, a same data set is used for all of the acts 26-32 either in real-time with scanning or in a post scan review. A static rendering using one set of data or volume may be used.

In act 24, estimates of velocity representing a volume of a patient are obtained. The estimates are obtained from memory or from scanning. For scanning, an ultrasound transducer is positioned adjacent, on, or within a patient. A volume scanning transducer is positioned, such as a mechanical wobbler or multi-dimensional array. For adjacent or on a patient, the transducer is positioned directly on the skin or acoustically coupled to the skin of the patient. For within the patient, an intraoperative, intercavity, catheter, transesophageal, or other transducer positionable within the patient is used to scan from within the patient. The user may manually position the transducer, such as using a handheld probe or manipulating steering wires. Alternatively, a robotic or mechanical mechanism positions the transducer.

The volume region of the patient is scanned, such as scanning an entire heart or portion of the heart from the esophagus or through another acoustic window. For example, the data represents at least a portion of the heart of a patient where the portion includes one or more vessels. Other organs (e.g., bladder) or parts of a patient may be scanned. The wobbler, multi-dimensional array, or other array generates acoustic energy and receives responsive echoes. In alternative embodiments, a one-dimensional array is manually moved for scanning a volume.

Spatial samples along one or more scan lines are received. Where the transmit beam insonifies just one receive scan line, then samples along that scan line are received. Where the transmit beam insonifies multiple scan lines, then samples along the multiple scan lines are received. To generate the samples for different receive beams, parallel receive beamformation is performed so that the different receive beams are sampled at a same time. For example, a system may be capable of forming two or more, tens or hundreds of receive beams in parallel. Alternatively, signals received from the elements are stored and sequentially processed. Spatial samples are acquired for a plurality of receive lines in the region of interest in response to one and/or in response to sequential transmit beams.

The scanning may be performed a plurality of times to cover the volume. The acts are repeated to scan different portions of the volume of interest. Alternatively, performing once acquires the data for the entire volume of interest.

The complete region of interest or field of view is scanned multiple times at different times. Scanning at different times acquires spatial samples associated with flow or motion. Any now known or later developed pulse sequences may be used. A sequence of at least two (flow sample count) transmissions is provided along each scan line. Any pulse repetition frequency, flow sample count, and pulse repetition interval may be used. The echo responses to the transmissions of the sequence are used to estimate velocity at a given time. The transmissions along one line(s) may be interleaved with transmissions along another line(s). With or without interleaving, the spatial samples for a given time are acquired using transmissions from different times. The estimates from different scan lines may be acquired sequentially, but rapidly enough to represent a same time from a user perspective. Multiple scans are performed to acquire estimates for different times.

The received spatial samples may be clutter filtered by a clutter filter. The clutter filtering is of signals in the pulse sequence for estimating motion at a given time. A given signal may be used for estimates representing different times, such as associated with a moving window for clutter filtering and estimation. Different filter outputs are used to estimate motion for a location at different times.

Color flow data or tissue motion data is generated from the spatial samples. Doppler processing, such as autocorrelation by a Doppler processor, may be used to estimate the velocity for each of the samples. In other embodiments, temporal correlation may be used. Another process may be used to estimate the flow data. Color Doppler velocities are estimated from the spatial samples acquired at different times. "Color" is used to distinguish from spectral Doppler imaging, where the power spectrum for a range gate is estimated. The change in frequency (e.g., Doppler shift) between two samples for the same location at different times indicates the velocity. A sequence of more than two samples may be used to estimate the velocity values. Estimates are formed for different groupings of received signals, such as completely separate or independent groupings or overlapping groupings. The estimates for each grouping represent the spatial location at a given time.

The estimation is performed for the different sampled spatial locations. For example, velocities for the different voxel locations in a volume are estimated from echoes responsive to the scanning. Multiple frames of flow data may be acquired to represent the volume of interest at different times.

The estimates may be thresholded. Thresholds are applied to the velocities and/or estimates of power of the flow. For example, a low velocity threshold is applied. Velocities below the threshold are removed or set to another value, such as zero. As another example, where the energy is below a threshold, the velocity value for the same spatial location is removed or set to another value, such as zero. Alternatively, the estimated velocities are used without thresholding.

One or more sets of data are obtained. The ultrasound data corresponds to beamformed data, detected data, and/or scan converted data. The ultrasound data represents a volume (e.g., N×M×O where N, M and O are integers greater than 1) of a patient. Data for multiple planar slices may represent the volume region. Alternatively, a volume scan is used.

The estimates of velocity are color flow data or tissue motion data. For examples herein, color flow data is used. To estimate the color flow, data representing blood, fluid, or flow of the patient is acquired. The estimates are for different locations or voxels within the volume.

The estimates of velocity are signed. The sign is a binary representation of the flow to or away from the transducer. The sign represents the direction of flow along the scan line. For example, flow away from the transducer is negative and flow towards the transducer is positive, or vice versa. The magnitude of the estimate indicates the rate of the flow while the sign indicates the direction.

In act 26, the estimates may be phase unwrapped by a processor or filter. If the velocity scale is set such that some of the velocities are aliased, the aliasing is removed by phase unwrapping. The phase unwrapping corrects the velocities, such as adding or removing phase by $2\pi$. Any phase unwrapping may be used. Sign changes, amplitude, spatial variance, or other information may be used to identify aliased values. The phase unwrapping is applied to the aliased values. The phase unwrapping produces unaliased or corrected velocity information.

If aliased estimates are not unwrapped, the termination of compositing due to sign change may cause a "black out" or termination at an incorrect estimate resulting in failure to composite flow of the same direction. Phase unwrapping may avoid this loss of information, allowing compositing to continue until a sign change due to actual change in flow direction is detected.

In act 28, the estimates are spatially filtering by a processor or filter. Low pass filtering is applied to smooth the estimates. The filtering is one dimensional, such as along the view direction used for rendering (e.g., along ray lines). Alternatively, the filtering is multi-dimensional, such as three-dimensional. The filtering is linear, direction counting, or other type of filtering. For direction counting, a majority of signs within the kernel centered over a given voxel or location is used to assign the sign to the estimate of that location.

The estimates are filtered for both direction (e.g., sign) and magnitude. Any size kernel may be used. By filtering the direction, variations in sign caused by noise may be removed, resulting in more consistent sign for the estimates. Sign changes along a ray line are more likely associated with actual change in flow direction rather than due to noise or aliasing.

As an alternative or in addition to spatial filtering, temporal filtering is applied. The estimates for a same location but different times are filtered.

In act 30, the directional flow data or estimates are volume rendered by a graphics processor or other processor. For direct volume rendering, ray lines are defined through the volume along a viewing direction. The view direction corresponds to a position of a virtual viewer relative to the volume. A processor receives an indication of the view direction from user interface operation or from data processing. For example, a user selects an orientation from which to view the volume. As another example, a processor selects the orientation based on the orientation of the volume relative to the patient. The user or processor may adjust the viewing direction to provide the desired view. The adjustment is performed by entering an angle, orienting a clipping volume, moving a line representing the viewing direction, or other mechanism.

The volume is volume rendered along the view direction. The volume rendering is a projection, surface, or other rendering. The type or other characteristics of the volume rendering are based on predetermined settings or user selections. For direct or projection rendering, conceptual ray lines are formed through the volume. The ray lines are parallel to the view direction. Alternatively, the ray lines diverge from a location of the virtual viewer to pass through the volume. The ray lines pass through or by voxels or locations of estimates. A ray line is provided for each pixel of an image to be rendered. In alternative embodiments, more or fewer ray lines than pixels may be used.

The estimates along each ray line are composited. The ray lines intersect voxels. To provide estimates on the ray line, surrounding estimates may be interpolated to the ray line. A nearest neighbor approach may be used instead. Alternatively, the intersected voxels are used without interpolation.

The estimates along the ray line are composited. Any compositing function may be used, such as alpha blending, averaging, or maximum intensity (magnitude). Progressing from estimates closest to the viewer to estimates further from the viewer, each new estimate is composited with the results from compositing previous estimates. For example in alpha blending, the estimates are combined in a recursive blending (infinite impulse response where a current sample is blended with a previous blended result) and opacities associated with the estimates are also combined in a recursive blending. As an example in maximum intensity, if the next estimate along the line has a greater intensity than the currently selected intensity, then the magnitude of the next estimate is selected. Otherwise, the previously selected magnitude is maintained and compared to any further next estimates. Any now known or later developed compositing may be used.

Figure 2:
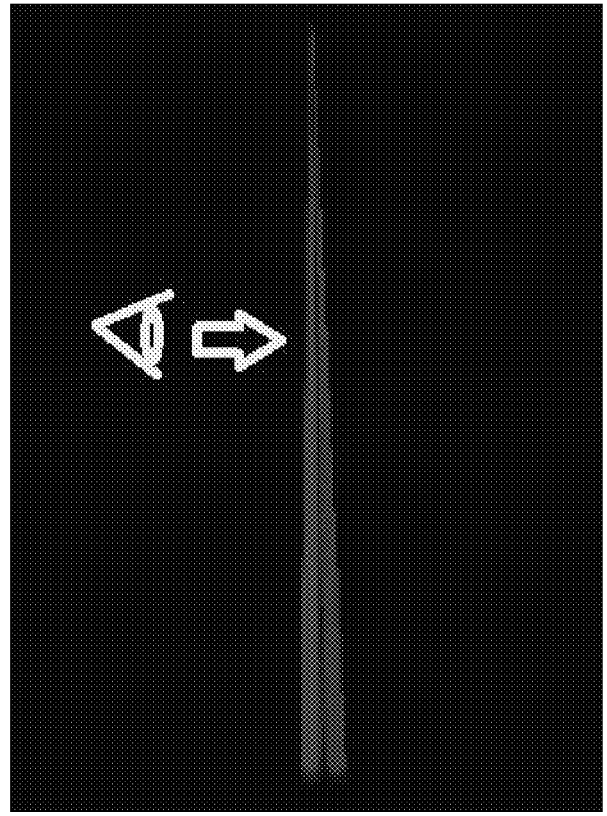
FIG. 2 shows an example arrangement of velocity data relative to a viewer.
Figure 3:
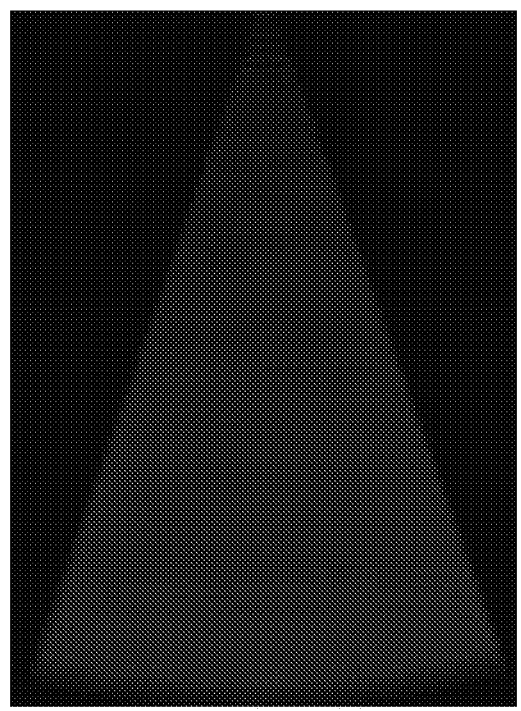
FIG. 3 shows a rendering of the velocity data of FIG. 2 with compositing regardless of direction of flow.

FIGS. 2 and 3 show an example of rendering. In FIG. 2, a volume of synthetic estimates of velocity is represented as RGB or color data. In alternative embodiments, estimates before color mapping are used. In the volume, two slabs are provided, one behind the other relative to the virtual viewer (i.e., eye) and the view direction (i.e., arrow). The two slabs are for different flow directions relative to the transducer (e.g., top of the Figure), so one is mapped red (towards the transducer) and the other is mapped to blue (away from the transducer) to represent the different signs of the estimates. Other colors may be used.

FIG. 3 shows a direct volume rendering using alpha blending from the view direction. The ray lines intersect estimates of different signs. As a result, the red and blue colors composite into a magenta hue (i.e., blend of red and blue). For compositing scalar values before color mapping, the compositing of estimates of different signs may result in incorrect magnitudes or direction. The direction for the rendered estimates or pixels may be incorrect or ambiguous regardless of rendering color mapped or scalar estimates.

To avoid or reduce the ambiguity caused by rendering directional information, a change in the sign of the estimates is detected in act 32 during the rendering of act 30. The graphics processor or other processor detects the sign change. As each estimate is selected for compositing, the sign of the estimate is checked. The sign for a given ray line is set based on the first encountered estimate along the ray line or based on a first group of encountered estimates along the ray line. For a group, the average or majority sign is used. "First" for the estimate or for the group is used in the sense of rendering from the viewer to a compositing plane at the back of the volume. The estimates closer to the viewer are composited before estimates further from the viewer.

After setting the sign for a given ray line, the sign for a next estimate along the ray line is compared to the sign for the ray line. If the sign is the same, the compositing is performed. If the sign is different, a change in the sign is detected. A single estimate or multiple estimates in a row with the different sign may be used to trigger detection of a change in the sign along the ray line. In one embodiment, during the traversal of a ray in a direct volume rendering of color Doppler velocity data, the flow direction of the current ray sample is compared to the direction of the previous ray sample.

The detection is performed for each ray line. The sign used for a given ray line is independent of the signs for other ray lines.

In act 34, other criteria are used with the detection of the sign change by the graphics processor or other processor. Using one or more other criteria, the detection of the sign change is limited to estimates having a significant contribution. For example, estimates with a sign change, but low opacity or low magnitude, may be composited since the effect is small or weak. If the opacity or magnitude is larger, then the contribution is greater, so the sign change is detected. In addition to a flow direction change, other criteria may be used to determine whether or not to stop the color Doppler compositing along the ray.

The other criterion is compared to a threshold. For example, a magnitude threshold is applied. If the estimate associated with a sign change is greater than or equal to the threshold, then the contribution may be significant, so the sign change is detected. The threshold is preprogrammed or may be set by the user.

Any other criteria may be used, such as opacity, luminance, flow data magnitude, difference in magnitude, the magnitude of the velocity change, the accumulated or sample-wise opacity, other sample data-related criteria, or combinations thereof. In addition to the criteria listed above, other velocity or non-velocity data-derived criteria may be used to decide when to stop compositing color Doppler velocity data along the ray.

In one embodiment, the criterion is opacity. In addition to the flow direction change, a check is performed to see if the opacity of the current sample to be composited is above a programmable threshold (e.g., 0 or other low opacity) or below a threshold for transparency. The compositing is stopped if the estimate has an opacity above the threshold or transparency below the threshold and a sign change. Adding the opacity criterion to the sign detection may avoid stopping compositing prematurely when a flow direction change is detected but the opacity is still low. If the opacity is low, the likelihood of good flow is low.

In another embodiment, the criterion is the magnitude. If the estimate of the current sample is above a programmable threshold (e.g., the velocity noise threshold), then the estimate is likely associated with actual flow and a sign change is detected. If below the threshold, then the estimate may be associated with noise so the sign change for that estimate is ignored in deciding to not stop compositing.

In yet another embodiment, the criterion is luminance or other measure of brightness. For color mapped estimates, the estimate has a corresponding luminance. If the luminance or other measure of brightness of the current estimate with a sign change is above a programmable threshold, then the estimate may have a significant contribution if composited so compositing is stopped. The quality of flow or motion may be inferred from the luminance. If low quality, then compositing may continue despite a sign change.

In yet another embodiment, the criteria is a difference in the absolute values of adjacent estimates or between a current to-be-composited estimate and the composited value. The difference is compared to a threshold (e.g., abs(abs(v1)−abs(v2)))>threshold). Not only must the flow direction change, but the amount of the flow direction change may also be used to decide whether or not to stop compositing. Small overall changes in direction may not result in an early ray termination.

In act 36, the contribution to the compositing of estimates beyond the detected change in sign is reduced by the graphics processor or other processor. For the estimate first associated with the change in sign and other estimates beyond that change relative to the virtual viewer, the contribution to the compositing is reduced as compared to the contribution if continuing to composite. Alternatively, the contribution of estimates of the opposite sign to the ray line is reduced, but estimates of the same sign as the ray line are composited without reduction.

The reduction occurs in response to detecting just the sign change. Alternatively, the reduction occurs in response to detecting the sign change where one or more other criteria are also satisfied. For example, reduction occurs in response to detecting a sign change and one or more of opacity above the threshold, the estimate being above the threshold, the luminance being above the threshold, and/or a difference being above the threshold. Where the contribution of the estimate is above a threshold and a sign change occurs, the compositing is reduced. When the contribution is below the threshold and a sign change occurs, the compositing is not reduced or is reduced less. When a sign change does not occur, the compositing continues without any reduction regardless of the contribution. Alternatively, contribution is considered.

Any reduction may be performed. For example, the compositing for that ray line is terminated. The compositing does not continue for any estimates regardless of sign beyond the estimate for which a sign change is detected. By terminating compositing along a given ray line, the compositing of the directional flow data is stopped. This early ray termination may save processing time. Other compositing, such as of B-mode information, along the ray line may or may not continue.

In another approach to reduction when rendering with alpha blending, the reduction is through altering of the opacity associated with the estimate and other estimates beyond the sign change or associated with any estimates of a different sign from the sign of the ray line. By setting the opacity to a small value (e.g., 0 or bottom 10% of opacity scale), the contribution of estimates with different flow from the ray line is reduced. Alternatively, the opacity of the last or deepest estimate along the view direction before the sign change is set higher (e.g., set to the maximum opacity) to prevent further processing along the ray line. Once the composited opacity reaches a maximum, then compositing may cease.

In act 38, an image is generated by the graphics processor or other processor. The volume rendering of act 30 creates pixel values for ray lines. The pixels form the image. Further processing may be performed, such as color mapping composited scalar values. The image is a representation of the volume, so is a three-dimensional representation for a two-dimensional display. The image represents the volume at a given time. Other renderings may represent the volume at other times, such as for a sequence of images. The image is of the volume rendered from the selected view point.

The image is of velocity in the volume. Only estimates of the velocity are used in rendering the image. Alternatively, other information, such as B-mode and/or power, are used in the rendering. For voxels or locations without velocity, B-mode information may be used in rendering. Alternatively, separate images are rendered and overlaid with each other or displayed side-by-side.

The image is displayed. The image is output to a display device for presentation to the user. A velocity image of the volume is three-dimensionally rendered to the display device, providing an image of the volume rendering.

Figure 4:
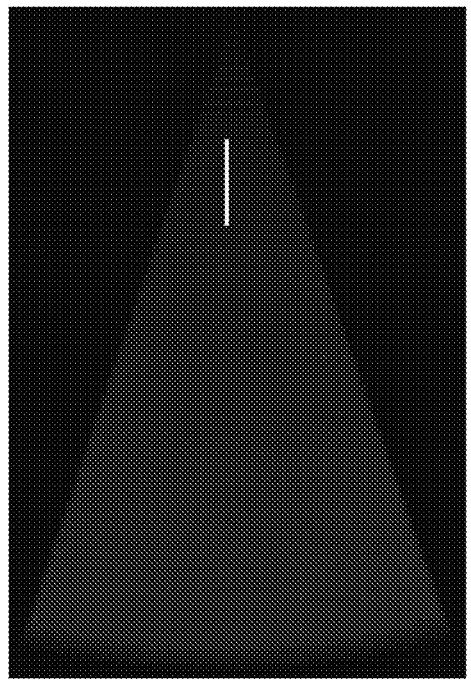
FIG. 4 shows a rendering of the velocity data of FIG. 2 with early termination due to sign change.

FIG. 4 shows the volume as represented in FIG. 2 rendered with termination based on sign change in combination with estimates being above a low velocity threshold. Since the estimates of FIG. 2 are synthetic, the low velocity threshold does not come into play, resulting in early termination just due to sign change. Following ray lines along the view direction going away from the viewer in FIG. 2 (direction of the arrow), all of the ray lines first encounter estimates with a same sign. Then, all of the ray lines encounter estimates with opposite signs. The estimates of the opposite signs are not included in the rendering due to detection of the sign change. As shown in FIG. 4, the result is a rendering of reddish hues rather than the magenta hues of FIG. 3. From the view perspective, only flow in one direction (e.g., flow towards the transducer) is visible so the coloring associated with that direction is maintained in the rendering.

Figure 5:
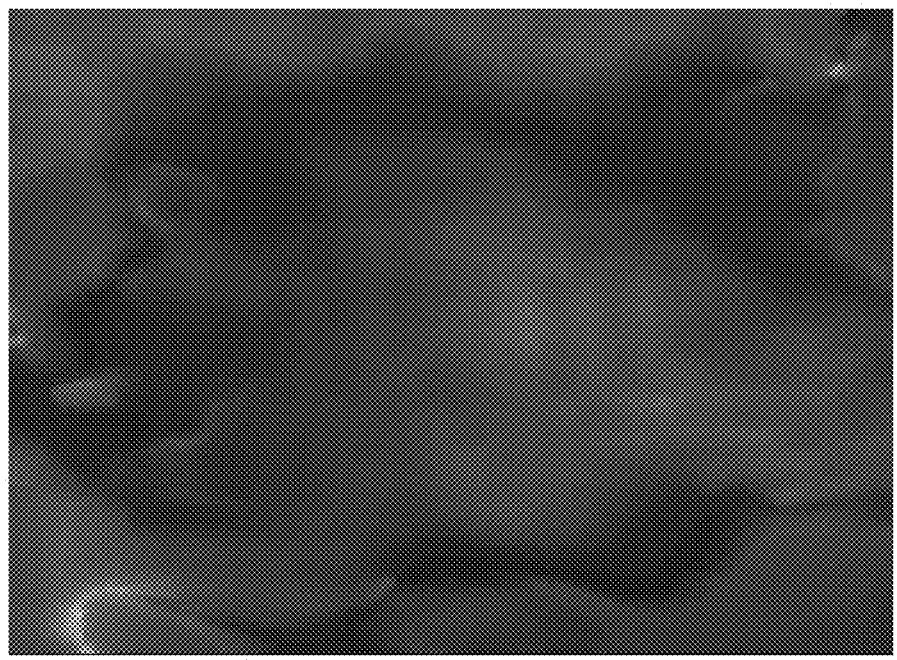
FIG. 5 shows an example rendering of a cardiac volume without early termination due to sign change.
Figure 6:
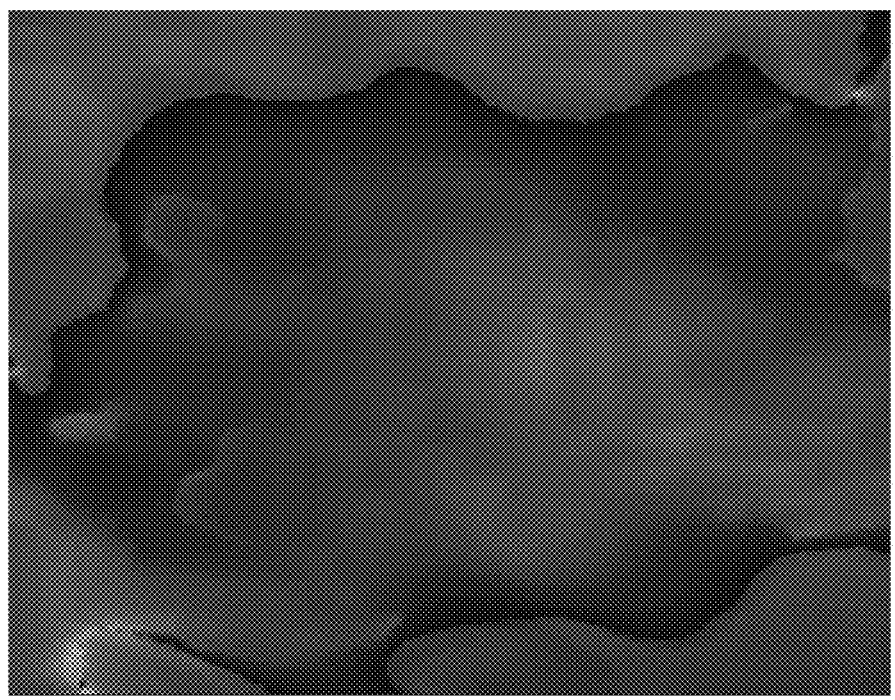
FIG. 6 shows an example rendering of the cardiac volume of FIG. 5, but with early termination due to sign change.

FIGS. 5 and 6 show another comparative example. FIG. 5 is rendered without considering any changes in the sign. Inter-hue mixing occurs at the boundaries between regions of positive flow (red) and negative flow (blue) in a cardiac color Doppler velocity volume data set. The magenta or purple color results at the boundaries between these flow regions. FIG. 6 shows the same volume rendered with termination of compositing where the sign changes, the RGB brightness or velocity is above a threshold, and the velocity difference (gradient) is above a threshold. Instead of magenta or purple at the boundaries, the expected reddish and bluish hues representing positive and negative flow are used.

Figure 7:
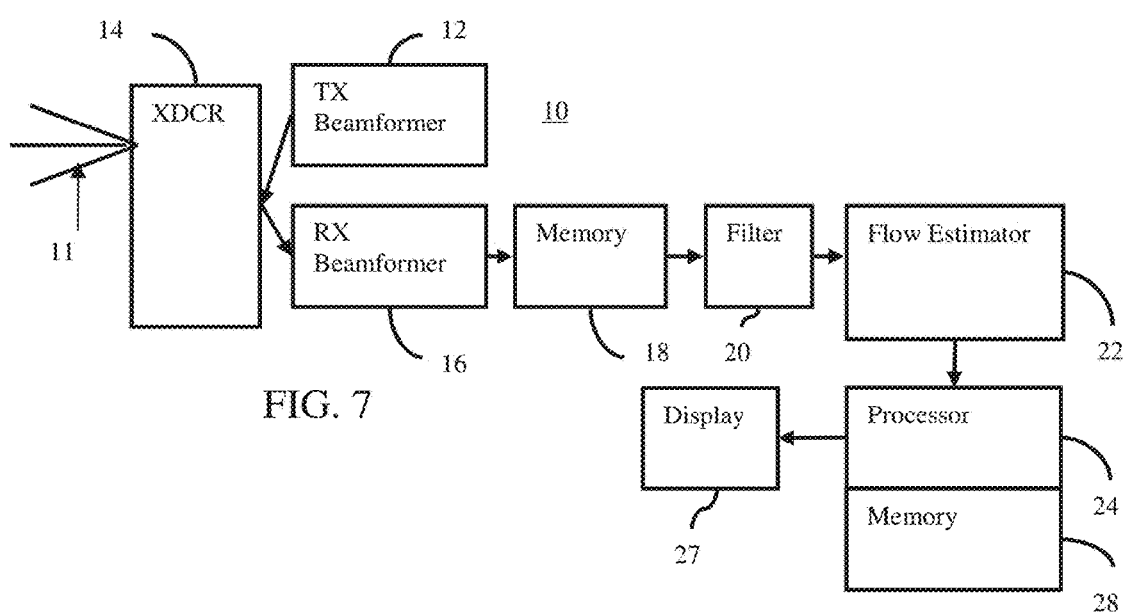
FIG. 7 is a block diagram of one embodiment of a system for volume rendering velocities in ultrasound.

FIG. 7 shows one embodiment of a system 10 for volume rendering in ultrasound. The system 10 includes a transmit beamformer 12, a transducer 14, a receive beamformer 16, a memory 18, a filter 20, a flow estimator 22, a memory 28, a processor 24, and a display 27. Additional, different or fewer components may be provided. For example, the system includes a B-mode detector. As another example, the flow estimator 22 and processor 24 are provided without the front-end components, such as the transmit and receive beamformers 12, 16. In one embodiment, the system 10 is a medical diagnostic ultrasound system. In an alternative embodiment, the system 10 is a computer or workstation. In yet another embodiment, the flow estimator 22 is part of a medical diagnostic ultrasound system or other medical imaging system, and the processor 24 is part of a separate workstation or remote system.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, a wobbler array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit and receive beamformers 12, 16 are a beamformer for scanning with the transducer 14. The transmit beamformer 12, using the transducer 14, transmits one or more beams to scan a region. Vector®, sector, linear, or other scan formats may be used. The receive lines and/or transmit beams are distributed in the scan region. The receive beamformer 16 samples the receive beams at different depths. Sampling the same location at different times obtains a sequence for flow estimation.

In one embodiment, the transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 digitally generates envelope samples. Using filtering, delays, phase rotation, digital-to-analog conversion and amplification, the desired transmit waveform is generated. Other waveform generators may be used, such as switching pulsers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal or other waveforms of a desired center frequency or frequency band with one, multiple or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles and/or combinations thereof. A transmit beam focus is generated based on these beamforming parameters.

The receive beamformer 16 is a preamplifier, filter, phase rotator, delay, summer, base band filter, processor, buffers, memory, combinations thereof or other now known or later developed receive beamformer components. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. In one embodiment, the beamform summer is configured to sum in-phase and quadrature channel data in a complex manner such that phase information is maintained for the formed beam. Alternatively, the beamform summer sums data amplitudes or intensities without maintaining the phase information.

The receive beamformer 16 is operable to form receive beams in response to the transmit beams. For example, the receive beamformer 16 receives one, two, or more (e.g., 16, 32, 64, or 128) receive beams in response to each transmit beam. The receive beams are parallel and offset or are nonparallel with the corresponding transmit beams. The receive beamformer 16 outputs spatial samples representing different spatial locations of a scanned region. Once the channel data is beamformed or otherwise combined to represent spatial locations along the scan lines 11, the data is converted from the channel domain to the image data domain. The phase rotators, delays, and/or summers may be repeated for parallel receive beamformation. One or more of the parallel receive beamformers may share parts of channels, such as sharing initial amplification.

For imaging motion, such as tissue motion or fluid velocity, multiple transmissions and corresponding receptions are performed for each of a plurality of substantially same spatial locations. Phase changes between the different receive events for each given location indicate the velocity of the tissue or fluid. A velocity sample group corresponds to multiple transmissions for each of a plurality of scan lines 11. The number of times a substantially same spatial location, such as a scan line 11, is scanned within a velocity sample group is the velocity sample count. The transmissions for different scan lines 11, different velocity sample groupings or different types of imaging may be interleaved. The amount of time between transmissions to a substantially same scan line 11 within the velocity sample count is the pulse repetition interval or pulse repetition frequency. Pulse repetition interval is used herein, but includes the pulse repetition frequency.

The memory 18 is video random access memory, random access memory, removable media (e.g. diskette or compact disc), hard drive, database, corner turning memory or other memory device for storing data or video information. In one embodiment, the memory 18 is a corner turning memory of a motion parameter estimation path. The memory 18 is configured to store signals responsive to multiple transmissions along a substantially same scan line. The memory 22 is configured to store ultrasound data formatted in an acoustic grid, a Cartesian grid, both a Cartesian coordinate grid and an acoustic grid, or ultrasound data representing a volume in a 3D grid.

The filter 20 is a clutter filter, finite impulse response filter, infinite impulse response filter, analog filter, digital filter, combinations thereof or other now known or later developed filter. In one embodiment, the filter 20 includes a mixer to shift signals to baseband and a programmable low pass filter response for removing or minimizing information at frequencies away from the baseband. In other embodiments, the filter 20 is a low pass, high pass or band pass filter. The filter 20 isolates velocity information from slower moving tissue and reduces velocities from fluids or, alternatively, reduces the influence of data from tissue while maintaining velocity information from fluids. The filter 20 has a set response or may be programmed, such as altering operation as a function of signal feedback or other adaptive process. In yet another embodiment, the memory 18 and/or the filter 20 are part of the flow estimator 22.

The flow estimator 22 is a Doppler processor or cross-correlation processor for estimating the color flow data. In alternative embodiments, another device now known or later developed for estimating velocity from any or various input data may be provided. The flow estimator 22 receives a plurality of signals associated with a substantially same location at different times and estimates a Doppler shift frequency, based on a change or an average change in phase between consecutive signals from the same location. Velocity is calculated from the Doppler shift frequency. Alternatively, the Doppler shift frequency is used as a velocity. The power and variance may also be calculated. Color flow data (e.g., velocity) is estimated for spatial locations in the scan volume from the beamformed scan samples. For example, the flow data represents a plurality of different voxel locations in a volume.

The flow estimator 22 may apply one or more thresholds to identify sufficient motion information. For example, velocity and/or power thresholding for identifying velocities is used. In alternative embodiments, a separate processor or filter applies thresholds. In other embodiments, the thresholding is applied after any motions suppression, such as by the processor 24.

The flow estimator 22 outputs frames of data representing the scan region at different times. The beamformed samples for a given flow sample count are used to estimate for a time. A moving window with overlap of the data is used to estimate for other times. Velocities for each location at different times are output.

The memory 28 is video random access memory, random access memory, removable media (e.g. diskette or compact disc), hard drive, database, or other memory device for storing color flow or other motion data, such as velocity data. The stored data is in a polar or Cartesian coordinate format. The memory 28 is used by the processor 24 for the phase unwrapping, filtering, rendering, sign change detection, early ray termination, or other acts described for FIG. 1. The starting velocities representing voxels in a volume of a patient for rendering are stored in the memory 28. Other data, such as phase unwrapping, filtered data, interpolated values, ray line designations, or rendering information may be stored in the memory 28.

The instructions for implementing the processes, methods and/or techniques discussed above are provided on non-transitory computer-readable storage media or memories, such as a cache, buffer, RAM, removable media, hard drive or other computer readable storage media, such as represented by the memory 28. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The processor 24 is a digital signal processor, a general processor, an application specific integrated circuit, field programmable gate array, control processor, digital circuitry, analog circuitry, graphics processing unit, graphics card, separate computer, workstation, combinations thereof or other now known or later developed device for volume rendering. The processor 24 operates pursuant to instruction provided in the memory 28, or a different memory for volume rendering for color Doppler imaging in medical diagnostic ultrasound.

The processor 24 receives color flow data from the flow estimator 22, the memory 28, and/or another source. In one embodiment, the processor 24 implements one or more of the algorithms, acts, steps, functions, methods or processes discussed herein, by processing the data and/or controlling operation of other components of the system 10. Additional or multiple processors may be used to implement various aspects of the algorithms.

The processor 24 or the flow estimator 22 performs phase unwrapping. Alternatively, the velocity scale is set to avoid aliasing.

The processor 24 or a separate digital filter spatially filters the velocities. The filtering is low pass filtering to remove noise or other information causing changes in sign that may not be accurate. The filtering (e.g., processor 24 or separate filter) is configured by design or programming to filter the velocities in sign and/or magnitude. The subsequent rendering and sign change detection is performed on the filtered velocities.

The processor 24 is configured by software and/or hardware to volume render an image of pixels from the velocities representing motion in the volume of the patient. The velocities being rendered are scalar values, such as values estimated by the flow estimator 22, or are color mapped values, such as RGB values. The processor 24 may convert the velocities into a regular three-dimensional grid for rendering. Alternatively, the processor 24 renders from the acoustic grid or the data is converted to a grid by another device.

In performing the volume rendering, the processor 24 defines ray lines along a viewing direction, interpolates the velocities to the ray lines, and composites the velocities of each ray line. To determine the value to use for a given pixel of a two-dimensional image, the velocities along a line at different depths for that pixel are combined. Alpha blending, maximum projection, or other direct volume rendering compositing may be used.

Rather than using all of the velocities equally along each ray line, the processor 24 may terminate the compositing or reduce the contribution in the compositing of some velocities. The processor 24 is configured to volume render an image of pixels from the velocities where contribution for each pixel from velocities of the volume is limited to the velocities of a same sign. For example, the compositing for one or more ray lines in the rendering is stopped when the sign changes for the velocities of the ray line. Velocities of a different sign or flow direction behind, relative to the virtual viewer or view direction for the volume rendering, are not used or their contribution to the rendered pixel is reduced. The processor 24 determines the sign of velocities with or without also determining other criteria (e.g., opacity, luminance, magnitude, difference in magnitude, or combinations thereof). Where the sign changes or where the sign changes and one or more other criteria are satisfied (e.g., compared to a threshold), the compositing is terminated or contribution is reduced.

By volume rendering, the processor 12 generates one or more three-dimensional representations of the volume. Each three-dimensional representation has a viewing angle relative to the volume. After any color mapping where the rendering is of scalar values, the resulting image has colors reflective of both the magnitude and direction of flow in the volume as viewed from the selected viewing direction.

The display 27 is a CRT, LCD, plasma, projector, monitor, printer, touch screen, or other now known or later developed display device. The display 27 receives RGB, other color values, or other motion values and outputs an image. The image may be a gray scale or color image. The image represents the region of the patient scanned by the beamformer and transducer 14. Where velocities occur in different directions along a given ray line, the velocities closer to the viewer or velocities of the same sign as velocities closer to the viewer are used for rendering on that ray line and velocities of other signs, unless contributing in an insignificant way, are not used.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for volume rendering in ultrasound, the method comprising:
    obtaining estimates of velocity at different locations distributed in three-dimensions in a patient, the estimates being signed for the velocity to and away from an ultrasound transducer;
    compositing the estimates along ray lines in a front to back direction relative to a view direction in three-dimensional rendering;
    during the compositing in the front to the back direction for at least one of the ray lines, detecting a change in sign of the estimates in sequence from the front to the back, the detecting of the change being from a comparison of a sign of one of the estimates to a sign of another of the estimates in the sequence;
    reducing contribution to the compositing of all of the estimates including and beyond the other estimate in the sequence for which the change in sign is detected, the reducing being in response to the detecting of the change and resulting in the contribution being less for all of the estimates beyond than without the reduction; and
    generating a velocity image from the three-dimensional rendering.

2. The method of claim 1 wherein obtaining comprises scanning with ultrasound and estimating the estimates from the scanning.

3. The method of claim 1 wherein compositing comprises alpha blending.

4. The method of claim 1 wherein compositing comprises interpolating the estimates for the locations along the at least one of the ray lines.

5. The method of claim 1 wherein detecting comprises establishing a sign of a first of the estimates and determining that the other estimate has a different sign than the sign of the one estimate from the comparison of the sign of the one estimate with the sign of the other estimate.

6. The method of claim 1 further comprising spatially low pass filtering, at least along the view direction, the estimates in sign and magnitude.

7. The method of claim 1 further comprising phase unwrapping the estimates.

8. The method of claim 1 wherein reducing comprises terminating the compositing for the at least one ray line in response to the detecting of the change in the sign of the estimates.

9. The method of claim 1 wherein reducing comprises altering opacity for the estimates beyond the change to be smaller.

10. The method of claim 1 further comprising comparing opacities of the estimates to a threshold, wherein reducing the contribution comprises reducing the contribution in response to both the change in the sign and the opacity above the threshold occurring.

11. The method of claim 1 further comprising comparing the estimates to a threshold, wherein reducing the contribution comprises reducing the contribution in response to both the estimate being above the threshold and the change in the sign occurring.

12. The method of claim 1 further comprising comparing luminances of the estimates to a threshold, wherein reducing the contribution comprises reducing the contribution in response to both the luminance being above the threshold and the change in the sign occurring.

13. The method of claim 1 further comprising calculating a difference in absolute value of the estimates, and comparing the difference to a threshold, wherein reducing the contribution comprises reducing the contribution in response to both the difference being above the threshold and the change in the sign occurring.

14. A system for volume rendering in ultrasound, the system comprising:
- a memory operable to store velocities representing voxels in a volume of a patient;
- a processor configured to:
  - volume render an image of pixels from the velocities where contribution for each pixel from velocities of the volume is limited to the velocities of a same sign, the processor being configured to volume render by compositing along ray lines for respective pixels and to stop compositing along any of the ray lines when the sign changes for the velocities of the ray line; and
- a display operable to display the image.

15. The system of claim 14 further comprising a spatial filter configured to filter the velocities in sign and magnitude, wherein the limiting to the velocities of the same sign is performed from the velocities output from the spatial filter.

16. The system of claim 14 wherein the processor is configured to determine the sign of the velocities from a direction and a contribution of the velocity based on opacity, luminance, magnitude, or combinations thereof.

17. In a non-transitory computer readable storage medium having stored therein data representing instructions executable by a programmed processor for volume rendering in ultrasound, the storage medium comprising instructions for:
- directly volume rendering directional flow data;
- detecting a flow direction change for directional flow data having a contribution to the volume rendering above a threshold; and
- stopping compositing of the directional flow data in the direct volume rendering when the flow direction change for the contribution above the threshold is detected.

18. The non-transitory computer readable storage medium of claim 17 further comprising displaying an image of the volume rendering.

19. The non-transitory computer readable storage medium of claim 17 wherein detecting comprises detecting the contribution as opacity, luminance, flow data magnitude, different in magnitude of the flow data, or combinations thereof.

* * * * *